United States Patent [19]

Iinuma

[11] Patent Number: 4,653,505
[45] Date of Patent: Mar. 31, 1987

[54] SYSTEM AND METHOD FOR MEASURING SOUND VELOCITY OF TISSUE IN AN OBJECT BEING INVESTIGATED

[75] Inventor: Kazuhiro Iinuma, Tochigi, Japan

[73] Assignee: Kabushiki Kaisha Toshiba, Kawasaki, Japan

[21] Appl. No.: 737,472

[22] Filed: May 24, 1985

[30] Foreign Application Priority Data

May 25, 1984 [JP] Japan ................................ 59-104695

[51] Int. Cl.⁴ .............................................. A61B 10/00
[52] U.S. Cl. ........................................ 128/660; 73/597
[58] Field of Search ............................ 128/660–661; 73/597–598, 625–626

[56] References Cited

U.S. PATENT DOCUMENTS

| | | | |
|---|---|---|---|
| 4,121,468 | 10/1978 | Glover et al. | 73/626 X |
| 4,252,025 | 2/1981 | Robinson | 73/626 X |
| 4,395,909 | 8/1983 | Steinberg et al. | 128/660 X |
| 4,523,468 | 6/1985 | Derkocs et al. | 73/598 |
| 4,566,459 | 1/1986 | Umemura et al. | 128/660 |

Primary Examiner—Kyle L. Howell
Assistant Examiner—Francis J. Jaworski
Attorney, Agent, or Firm—Finnegan, Henderson, Farabow, Garrett & Dunner

[57] ABSTRACT

A system and method for measuring the sound velocity of the tissue within an object to be investigated. A pulse of ultrasonic energy is transmitted along a steered transmitting beam into the object by a first sub-array of transducer elements that are a distinct part of an array of transducer elements. The echoes of the pulses return to the array along a steered receiving beam activated by a second sub-array of transducer, and the system measures the propagation time for the pulse to leave and return to the array. The average sound velocity within the object can be determined from the measured propagation time and the known geometric characteristics of the array, sub-array, and steered angles. The system and method can also be modified to determine the sound velocity of an inner tissue body, such as a lever, within a larger object, such as a human body, being investigated.

15 Claims, 7 Drawing Figures

(a)

(b)

(c)

(d)

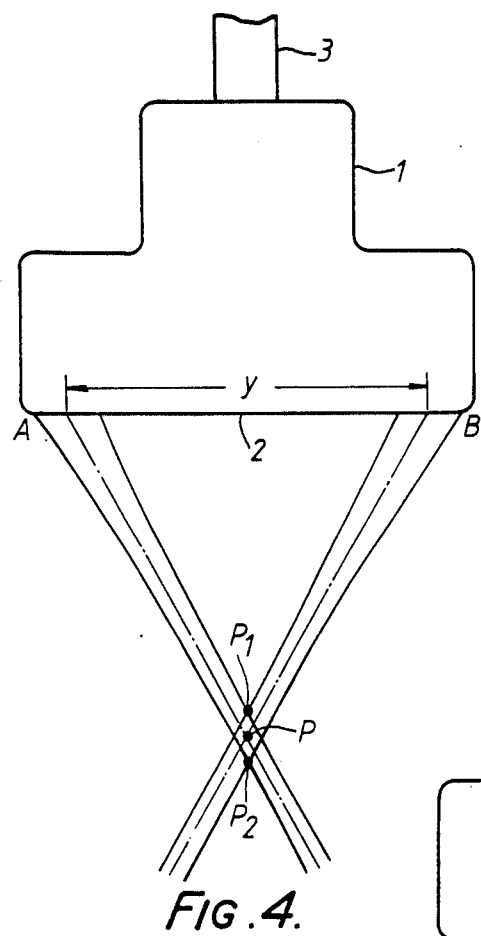
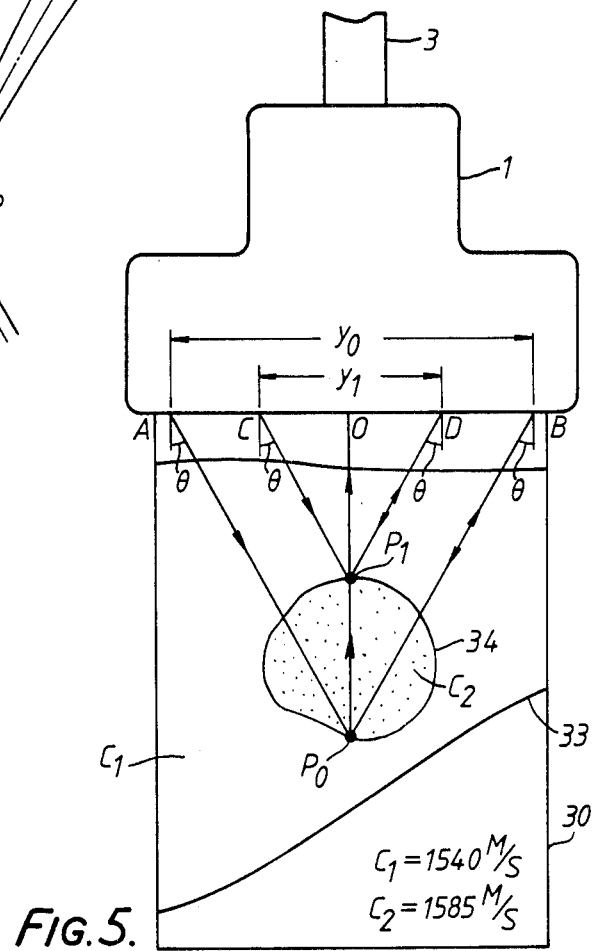
FIG. 4.
FIG. 5.

SYSTEM AND METHOD FOR MEASURING SOUND VELOCITY OF TISSUE IN AN OBJECT BEING INVESTIGATED

BACKGROUND OF THE INVENTION

1. Field of the Invention

This invention relates to a system and method for examining the tissue of an object to be investigated and is especially directed to in vivo measurement of the sound velocity of the tissue. Through such measurement, the user of the system and method can determine the nature of the tissue and often perform medical or scientific diagnosis.

2. Description of the Prior Art

Nishimura N. et al., "Measurement of Sound Velocity as a Diagnostic Tool Diffuse Liver Diseases," Japanese Journal of Medical Ultrasonics, 44-B-5, May 1984 shows a technique of measuring sound velocity of liver with two single transducers disposed at both ends of a linear array transducer. These two single transducers are disposed so that their beams cross within the liver. An ultrasonic pulse and its echo propagate from one single transducer through that cross point and to the other transducer. The propagation time taken by the pulse to travel that path is measured. The average sound velocity through the propagation path is computed from the propagation time, the distance between the two transducers, and the angles of propagation defined by the placement of the transducers. In this past technique, however, it is difficult to measure different paths of travel without physically moving one or both transducers. It is also difficult to achieve good contact with the surface of the object because the single transducers cannot be laid flat against the surface of the objects being investigated but instead must be angled. This problem becomes worse whenever the intersection point of the transducer's axes is near one or both transducers.

SUMMARY OF THE INVENTION

It is an object of the present invention to provide a system and method for measuring sound velocity of the tissue of an object using an ultrasonic beam transmitted from an ultrasonic transducer array.

Another object is to provide a system and method for measuring sound velocity of the tissue of an object using a transducer that can be laid flat against the surface of the object.

It is another object of the present invention to provide a system and method for measuring sound velocity of tissue of an object along a variety of paths within the object.

It is further object of the present invention to provide a system and method for measuring sound velocity of tissue within a particular portion of an object.

It is still a further object of the present invention to provide a system and method for measuring sound velocity of tissue within a particular portion of an object by measuring data representative of several sound velocities and cancelling all of the data except that representing the sound velocity within the particular portion.

Additional objects and advantages of the invention will be set forth in part in the description which follows, and in part will be obvious from the description, or it may be learned by practice of the invention. The object and advantages may be realized and attained by means of the elements and combinations particularly pointed out in the appended claims.

To achieve the objects and in accordance with the purpose of the invention, as embodied and broadly described herein, the system of this invention comprises an array of transducer elements spaced at predetermined intervals for transmitting pulses into the object and receiving echoes of the pulses reflected from the object, the array including a first sub-array of transducers and a distinct second sub-array of transducers, the first and second sub-arrays being separated by a predetermined distance, transmitting means coupled with the array for exciting the first subarray to direct pulses toward the object along a transmitting beam; receiving means coupled with the array for causing the second sub-array of transducers to receive echoes of the pulses along a receiving beam, beam steering means coupled with the first and second sub-arrays for activating said transducers at predetermined time delays to steer at least one of the transmitting beam and the receiving beam at an angle so that the transmitting beam and the receiving beam intersect at a point within the tissue; time measuring means coupled with the first and second sub-arrays for measuring the propagation time between the moment a pulse is transmitted by the first sub-array along the transmitting beam and the moment it is received by the second sub-array along the receiving beam, and computing means coupled with the time measuring means for determining the sound velocity of the tissue.

According to the present invention, the system and method of this invention permits a measurement of sound velocity of any tissue of an object, even if the tissue is in an internal organ. The system includes an array of ultrasonic transducers which can provide a B-mode image of the object. In addition to that, the array of ultrasonic transducers of this invention provides an ultrasonic transmitting beam and an ultrasonic receiving beam which intersect at a point within the object. The ultrasonic transmitting beam is transmitted from a first sub-array of ultrasonic transducers which are a part of the array. Echos reflected from the ultrasonic receiving beam are received by a second sub-array of the ultrasonic transducers. This second sub-array is another part of the array and is apart from the first sub-array. Both, or at least one, of the ultrasonic transmitting and receiving beams are steered so that they intersect at a selected point located within the object. The first sub-array transmits ultrasonic pulses along the ultrasonic transmitting beam. The ultrasonic pulses are scattered from the intersection point of the transmitting and receiving beams and are received by the second sub-array along the ultrasonic receiving beam. The system measures the time period from the transmission of an ultrasonic pulse by the first sub-array to the reception of the pulse by the second sub-array. The path length along which the ultrasonic pulse propagates is geometrically defined by the distance between the first and second sub-array and the steering angles of both the ultrasonic transmitting and receiving beams. The average sound velocity of the propagating pulse along this path can be calculated by dividing the path length by the time period.

The above system and method accurately measures the sound velocity of an object having a single type of tissue having the same sound velocity throughout. At times, however, an object may have several different tissue bodies, and it may be desirable to determine the sound velocity within a particular inner tissue body positioned inside the object and surrounded by different tissue. For example, an internal organ of a person being investigated would fall within this category. The inventors have designed and developed a system and apparatus to measure the sound velocity within such a particular inner tissue body. In that system and method, two sound velocities are measured to determine the sound velocity in the inner tissue body. In one measurement the ultrasonic transmitting and receiving beams intersect at a point within the inner tissue body to be examined. The beams therefore travel through both the inner tissue body and the tissue of the object between the inner tissue body and the array of transducers located on the surface of the object. A second measurement is made so that the transmitting and receiving beams intersect outside the inner tissue body at a point located approximately at the outer boundary of that inner tissue body, so that the pulses do not travel through the inner tissue body. The measurement of these two second velocities can be compared to define the sound velocity in the inner tissue body by mathematically cancelling the sound velocity of the portions on the beam path that are outside the inner tissue body.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWING

FIG. 4 is a schematic drawing illustrating the patterns of the transmitting and receiving beams provided by the embodiment shown in FIG. 2;

FIG. 5 is a schematic diagram illustrating the principles of the present invention applied to measure the sound velocity within an inner tissue body;

DESCRIPTION OF THE PREFERRED EMBODIMENT

Reference will now be made in detail to the present preferred embodiments of the invention, examples of which are illustrated in the accompanying drawings.

Figure 1:
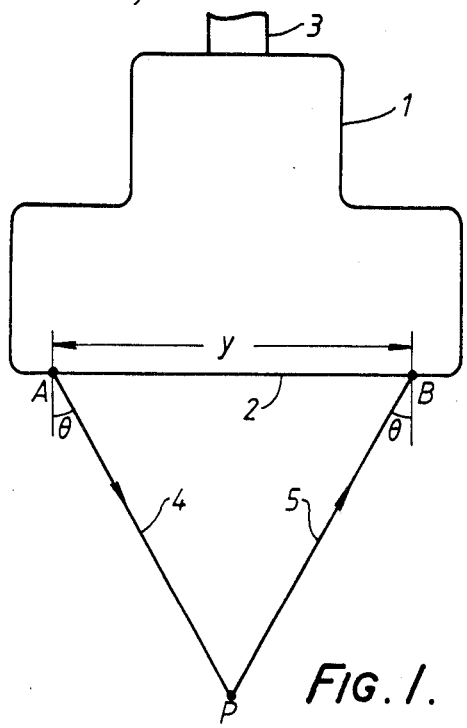
FIG. 1 is a schematic diagram showing an array of transducers of the present invention generally and illustrating the basic principle of the present invention.

FIG. 1 is explanatory of the basic principle applied by the present invention. In FIG. 1 an ultrasonic transducer 1 is connected to a transmitter and receiver (not shown) through a cable 3. The ultrasonic transducer 1 includes an array of ultrasonic transducers elements provided in its bottom surface 2. In use, the bottom surface 2 of transducer 1 is placed on a surface 6 of an object to be investigated. The transducer 1 transmits ultrasonic pulses into the object and receives echoes of the pulses that return from the object.

The transducer of the present embodiment performs two kinds of scanning. One is the well-known B-mode scanning which displays a tomogram of the object under investigation. In the B-mode scanning, for example, a plurality of parallel beams are scanned in a plane within the object. Echoes received along these parallel beams are modulated into brightness according to their intensities. The distributions of the brightness on a video display provide a tomographic image of the object. These parallel beams can be sequentially scanned in the same plane to obtain the tomographic image in real time. When a B-mode image is used with the present invention, the resultant tomographic image preferably is frozen on a monitor so that the image can be referenced during the measurement of sound velocity.

The other form of scanning performed by the present invention is beam scanning which is taken to measure the sound velocity of tissue within the object. In this scanning, ultrasonic pulses are transmitted from position A at one end of the array toward a point P along a steered transmitting beam 4. The transmitting beam 4 is steered at an angle $\theta$. The echoes of these pules that are scattered from point P are received at position B at the other end of the array along a steered receiving beam 5 which crosses with beam 4 at the point P. The transmitting and receiving beams are shown to be steered at the same angles, but could be steered at a wide variety of angles, as long as the transmitting and receiving beams ultimately intersect within the object. In other words, the ultrasonic pulses propagate on propagation path A-P-B. The present invention measures the propagation time T of the ultrasonic pulses along that path.

The average velocity C of sound through the propagation path A-P-B shown in FIG. 1 can be written as follows:

$$C = y/(T \cdot \sin \theta) \tag{1}$$

where y is the distance position A and B; T is the propagation time required for a pulse to leave the transducer at point A, go to point P within the object, and return to the transducer at point B; and $\theta$ is the steered angle of both beams 4 and 5. If the steering angles of beams 4 and 5 are not the same, the equation defining the average velocity C would be different but could be readily derived from known geometric relationships.

By solving the above equation, the average velocity C can be obtained. To solve the equation, however, one must obtain additional information and provide a system and method which overcomes the problems by the above described general principle. First, the angle $\theta$ of the transmitted and receiving beams are unknown, since they are a function of the unknown sound velocity within the object. Second, most objects do not include a single point reflector P which receives and reflects pulses. Therefore, some improvements are necessary to reduce to practice the measurement of sound velocity derived from equation (1).

Figure 2:
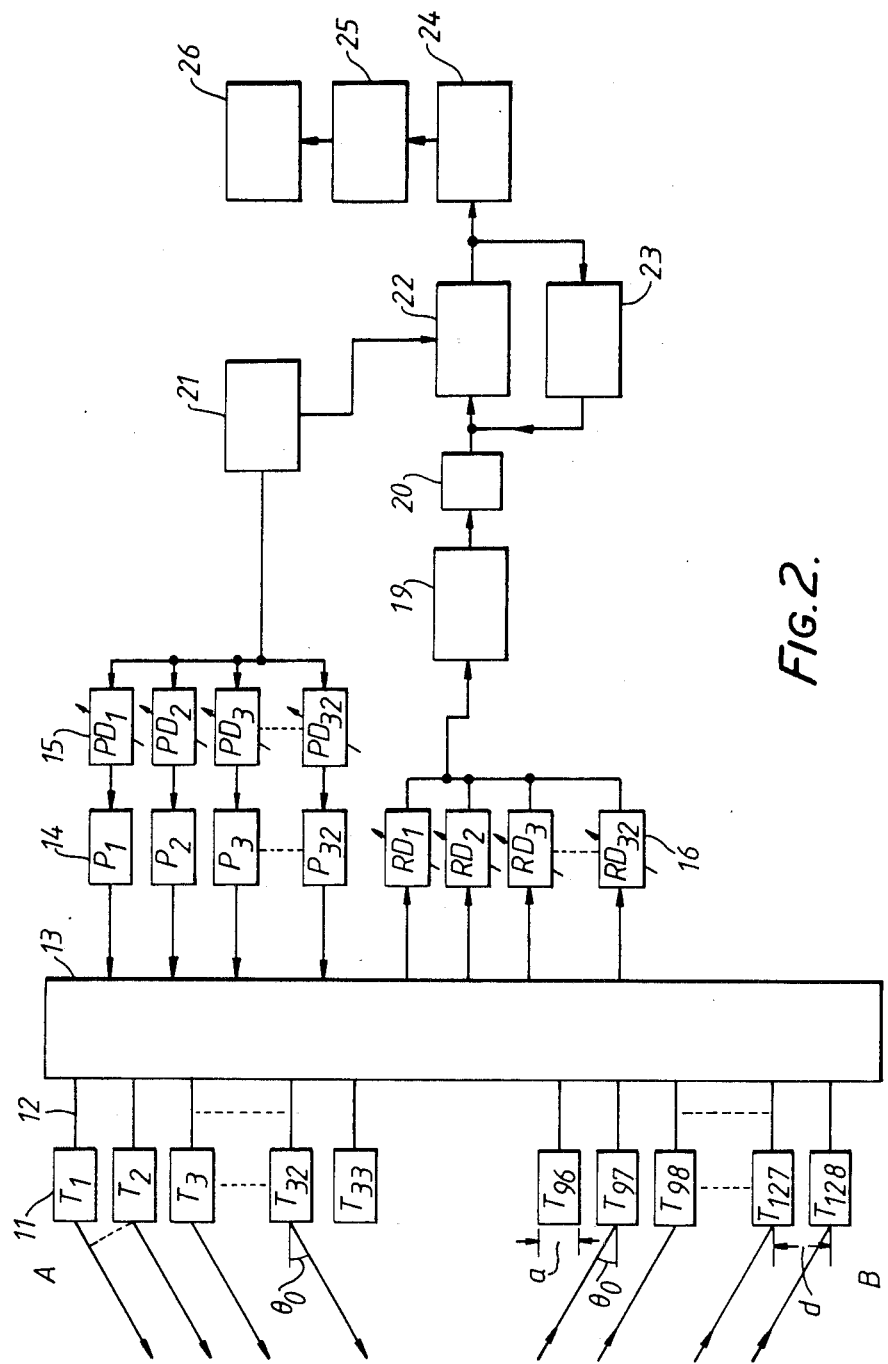
FIG. 2 is a block diagram illustrating an embodiment of an apparatus of the present invention.

A preferred embodiment of the present invention which provides the necessary improvements is shown in FIG. 2. In FIG. 2, an array of ultrasonic transducer elements 11 is arranged in the bottom surface 2 of the ultrasonic transducer 1. In the particular embodiment shown, the array 11 includes 128 transducer elements (T1 to T128). Each of the transducer elements is capable of transmitting an ultrasonic pulse when voltage is supplied to it and converting received echoes of pulses into electrical signals. In the preferred embodiment, these elements (T1 to T128) have a width of 0.45 mm and are juxtaposed in a row at an interval d of 0.5 mm. The voltages supplied to some of the elements (T1 to T128) and electrical signals converted by them are transmitted and received, respectively, through cables 12 which are connected to them. A clock pulse generator 21 generates 10 MHz clock pulses. These clock pulses are divided into 4 KHz rate pulses. In the preferred embodiment, these rate pulses are supplied to 32 transmitting delay lines 15. These delay lines 15 produce rate pulse delay times to steer the ultrasonic transmitting beam along a preselected steering angle. In preferred embodiment, delay lines 15 can produce variable delay times to thereby change the steered angle as desired. Moreover, delay lines 15 can also provide the transducers with delay times that focus the transmitted beam electronically at a given target within the object to be investigated.

In the preferred embodiment, the delayed rate pulses are supplied to 32 pulsers 14. The pulsers 14 generate high voltage pulses to excite the transducer elements. Outputs of these pulsers 14 are supplied to multiplexer 123 which in turn selects, for example, the elements T1 to T32 at the position A and connects pulsers 14 to them. The elements T1 to T32 are then excited with the delayed rate pulses and produce the desired ultrasonic pulses. The phased array 11 contacts with the surface of the object 6 through a coating material (not shown), and the desired ultrasonic pulses and resultant steered beam generated by the elements are transmitted into the object.

The delayed time $\tau_0$ between adjacent elements is defined by the following equation:

$$\tau_0 = (d/C_0) \cdot \sin \theta_0 \quad (2)$$

where $\theta_0$ is the desired transmitting angle, d is the distance between adjacent transducers, and $C_0$ is the average sound velocity of normal tissue, which is approximately equal to that in water, i.e. 1530 m/s. To steer the beams at an angle $\theta$, the delay lines 15 are set so that each element is driven by the delayed time difference $\tau_0$. Thus, the pulse delay eignals PD1=0, PD2=$\tau_0$, PD3=$2\tau_0$, and PD32=$31\tau_0$ are given to the respective delay lines 15 as delayed times. The ultrasonic pulses produced by these delayed time differences propagate along an ultrasonic transmitting beam steered at angle $\theta_0$.

If the sound velocity of tissue of the object 6 is $C_0$, the ultrasonic transmitting beam actually propagated through the object propagate at the angle $\theta_0$. Usually, however, the actual sound velocity C within the object is different from $C_0$. The angle $\theta$ along which the beam actually propagates is derived from Snell's law as follows:

$$\sin \theta / C = \sin \theta_0 / C_0 \quad (3)$$

After the ultrasonic pulses are sent towards the object, the multiplexer 13 in the preferred embodiment selects, for example, 32 elements T97 to T128 at the position B and connects them to receiving delay lines 16. Echo signals received by the elements T97 to T128 are delayed in the same manner as the transmitted signals. Thus, echo delay times of the receiving transducers are given as RD1=$31\tau_0$, RD2=$30\tau_0$, and RD32=0. These delayed echo signals are then summed up and supplied to receiver 19. By applying the delay time, the elements T97 to T128 receive echoes in direction $\theta_0$(or $\theta$), if the sound velocity of tissue is $C_0$(or C).

The receiver 19 amplifies and detects the summed echo signals, and A/D converter 20 converts the outputs of the receiver 19 into digital signals. The digital signals are stored in memory device 22. The memory device 22 determines what address to store the data in accordance with the timing of the 10 MHz of the clock pulse which also serves as a trigger of the rate pulse. Therefore, the measuring resolution of the embodiment shown in FIG. 2 is 100 n sec.

The peak value of the stored digital signals received by the second sub array and stored by the memory device represents the echo reflected at the point P. Wave analysis circuit 24 detects time, i.e. address, of the peak in the memory device 22. This time between the transmitted pulse and this peak is the propagation time T. The equation (1) can be rewritten from equations (3) and (2) as follow:

$$C = \sqrt{yC_0/(T \cdot \sin \theta_0)}$$

$$C = \sqrt{y \cdot d/T \cdot \tau_0}$$

The values of y, d and $\tau_0$ are known, and the value of T is measured by the present invention. Therefore, a computation circuit can be designed to compute the sound velocity C from these known values and then display the computed value of C on display 26.

When the present invention is used in B-mode scanning, the multiplexer 13 causes a sub-array in the array to transmit pulses and receive their echoes along the same beam axes. These echo signals from the A/D converter 20 are stored on locations in a frame memory (not shown). The data in frame memory can be placed in a TV format to display a tomographic image on a monitor (not shown). In the preferred embodiment, a frozen tomogram is displayed from the information on the frame memory so that the tomogram can be reviewed at the same time the system is used to measure the sound velocity of tissue.

Figure 3:
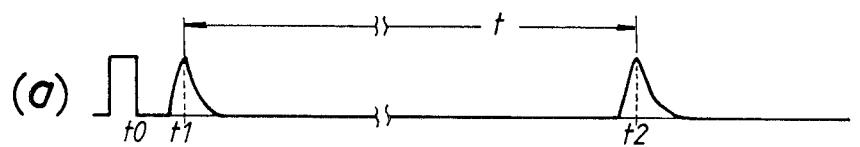
FIGS. 3(a)-3(d) are timing charts illustrating the transmission and reception of pulses by the first and second sub-arrays, respectively, for various tissue types and signal processing techniques and showing graphically the time period measured by the embodiment shown in FIG. 2.
Figure 3:
Figure 3:
Figure 3:
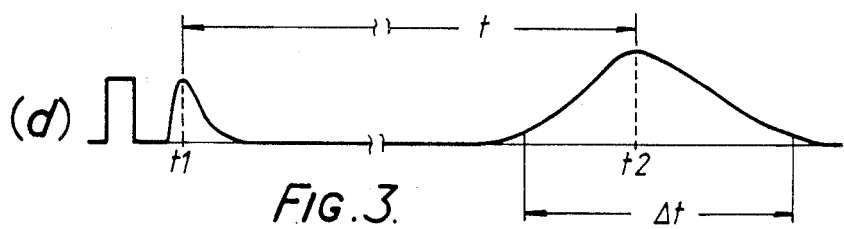

FIG. 3 shows a timing chart illustrating the transmission and reception of pulses by respective sub-arrays and showing graphically the time period measured by the present invention. The ultrasonic pulse transmitted by the sub-array at point A peaks at time t1 which is slightly after the time when the beam is initially pulsed.

In circumstances where there is a point reflector P at the intersection point of the ultrasonic transmitting beam and the ultrasonic receiving beam, the system will detect a fairly distinct echo signal which has a peak at t2, as shown in FIG. 3(a). In that circumstance, the propagation time t is obtained as the interval between times t1 and t2. When investigating a particular object, it may be possible to adjust the ultrasonic transducer so that the two beams intersect at a natural point reflector, such as a blood vessel in the liver. Generally, however, it is difficult to find such a point reflector during a clinical measurement. As described below, the present invention can measure the sound velocity of tissue in an object, even if there is no point reflector within the object.

FIG. 4 illustrates the beams in an object which does not contain a single point reflector. For example, when a liver is examined, the intersection of the two beams may be surrounded by uniform liver tissue. As shown in FIG. 4, the beams each would have some width and would not intersect at a distinct point. Accordingly, the echoes would reflect from the liver tissue at the cross section defined by the intersecting widths of two beams. The signal arriving most quickly would be the signal returning from point P1, and the latest arrived signal would return from point P2. In this case, as shown in FIG. 3(b), the waveform of echoes would be scattered and uneven since they are received as a number of successive signals. Therefore, it is difficult to detect the peak. One manner of overcoming this difficulty is to sum the echoes in order to obtain a smoothed wave shape. It is further preferable to shift the position of the point P slightly, take several readings around point P, and average the resultant values of the sound velocity. Alternatively, the echoes may be processed with peak hold process at each address to smooth them. By smoothing the received signals by one or more of the above methods or their equivalents, the wave shape becomes smoothed as shown in FIG. 3(c). Furthermore, it is possible to obtain the completely smoothed wave shape (d) by performing a curve fitting utilizing, for example, the least squared method. The resultant curve would then look like that shown in FIG. 3(d). In all cases, the propagation time t is represented as $t = t2 - t1$.

The embodiment described above can operate under a wide possibility of variations. As an example, the beam width at the intersection is about 2 mm when the ultrasonic frequency is 3.5 MHz and the distance y between the positions A and B is 48 mm. In this situation the propagation difference time $\Delta t$ between the propagation times through P1 and P2 is about 4.5 μs. The propagation time t is about 62.7 μs where unknown sound velocity C is equal to the sound velocity $C_0$ of water and the steering angle is 30 degrees. Since the accuracy of the measurement is less than one tenth (1/10) of the propagation difference time $\Delta t$, the probable error of measuring sound velocity is within 10 m/s.

The sound velocity measured by above disclosed system and method is the average sound velocity of the path A-P-B shown in FIG. 1. The average sound velocity of tissue can be measured by the above system for tissue close to the surface of the object. It can also measure the average sound velocity for beams intersecting at greater depths. The depth and position of intersection point P, and therefore the tissue through which the beams travel, can be varied as desired. It should be clear, however, that the above system and method does not measure the sound velocity of a separate tissue body located within the object. It times, it is desirable to determine the sound velocity of such tissue or to compare the sound velocity of an inner tissue body with the tissue surrounding the body. For example, that information might allow a person to diagnose whether the inner tissue body is cancerous or benign. As explained below, the inventor has found that it is possible to measure sound velocity of an inner tissue body of an object by utilizing the system shown in FIG. 2.

The application of the present invention to measure the sound velocity within an inner tissue body is illustrated in FIG. 5. The ultrasonic transducer 1 provides a tomographic image of, for example, a human liver and the tissue surrounding that liver. The tomogram might display the skin, fat and muscles layer 31, liver 32, diaphram 33 and an abnormal tissue body 34 like a cancer within the liver 32. It is critically significant to measure sound velocity of the abnormal tissue 34 to determine whether it is cancerous.

To obtain the sound velocity within the inner tissue body 34, an operator selects transmitting positions A, C, D and B, and the receiving positions O, B and D. The steering angles of the beams are selected so that the cross points P1 and P0 are located just above and below the abnormal tissue 34. This placement of the points P1 and P0 will allow the pulses to travel through the entire length P1-P0 of the inner tissue body being examined. It should be clear, however, that the point P0 can be placed within the inner body so that the sound velocity is determined within a selected portion of the inner tissue body. In the example shown in FIG. 5, the steering angles $\theta$ are the same for each transmitting beam and receiving beam. The use of a same angle simplifies the mathematical determination of the average sound velocity of the inner tissue body, but if desired, different steering angles can be selected for the various beams. The multiplexer 13 adjusts these transmitting and receiving positions in the array. When the receiving beams OP1 and OP2 are selected, the delayed times RD1 to RD32 of receiving delay lines 16 are set. The round-trip propagation time $t_l$ between P1 and P0, shown in FIG. 5, is obtained from the following measurement:

$$t(AB) = t(AP0) + t(P0B)$$

$$t(A0) = t(AP0) + t_l/2 + t(P10)$$

$$t(B0) = t(BP0) + t_l/2 + t(P10)$$

$$t(CD) = t(CP1) + t(P1D)$$

$$t(C0) = t(CP1) + t(P10)$$

$$t(D0) = t(DP1) + t(P10) \tag{5}$$

where t(AB) represents the propagation time between A and B.

The round-trip propagation time $T_l$ is as follows:

$$t_l = [\{t(A0) + t(B0) = t(AB)\} - \{t(C0) + t(D0) - t(CD)\}] \tag{6}$$

The average sound velocity C between the positions P1 and P0 can be determined as follows:

$$C_l = 2 \times l/t_l \tag{7}$$

$$= (y0 - y1)/(t_l \cdot \tan \theta)$$

where y0 is the distance between the positions A and B, y1 is the distance between the positions C and D, and X is the distance between the cross points P0 and P1. The value $\theta$ is approximated from the average sound velocity of normal liver portion using equation (3) as follows:

$$\theta = \sin^{-1}\{(C/Co) \cdot \sin\theta_0\} \tag{8}$$

Although the equation (7) is not exact, its error is small if the steering angle is near a right angle (90 degrees).

The invention is not limited to the particular embodiment shown in FIG. 5 or the mathematical calculations shown above. Instead, a variety of paths and angles can be selected as long as one point $P_1$ is proximate the outer periphery of the inner tissue body 34 so that the pulses do not travel through the inner tisue body and the other point $P_0$ is choosen so that the pulses travel through at least part of the inner tissue body. The value of the average sound velocity C can then be derived from the known values of the choosen distances and angles. For example, in a case where the abnormal tissue 34 is small or the partial path X is short, the partial sound velocity C can be approximated by the difference between the propagation times of the path A-Po-B and C-P1-D or A-Po-O and C-P1-O because one path is through the partial tissue and the other path is not. Generally, fat layers reduce the sound velocity considerably. The sound velocity of the tissue surrounding the inner tissue body is also different than that of the inner tissue body. In this measuring method or system the sound velocity of fat layer, or other layers, can be approximately cancelled by setting $P_0$ at a lower portion of the inner tissue body 34 and setting $P_1$ at the upper portion of the inner tissue body.

In the preferred use of the above system and method, the selected paths and intersections are preferably overlayed on the B-mode tomogram of the object to facilitate the diagnosis. The resultant display is illustrated by FIG. 5.

Figure 6:
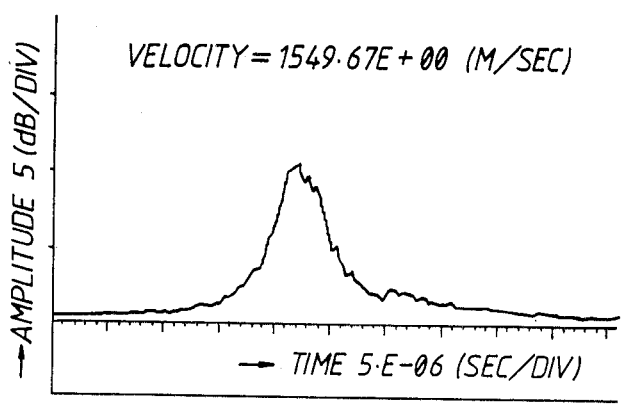
FIG. 6 is a graph illustrating the waveforms of receiving echoes obtained by the embodiment shown in FIG. 2.
Figure 7:
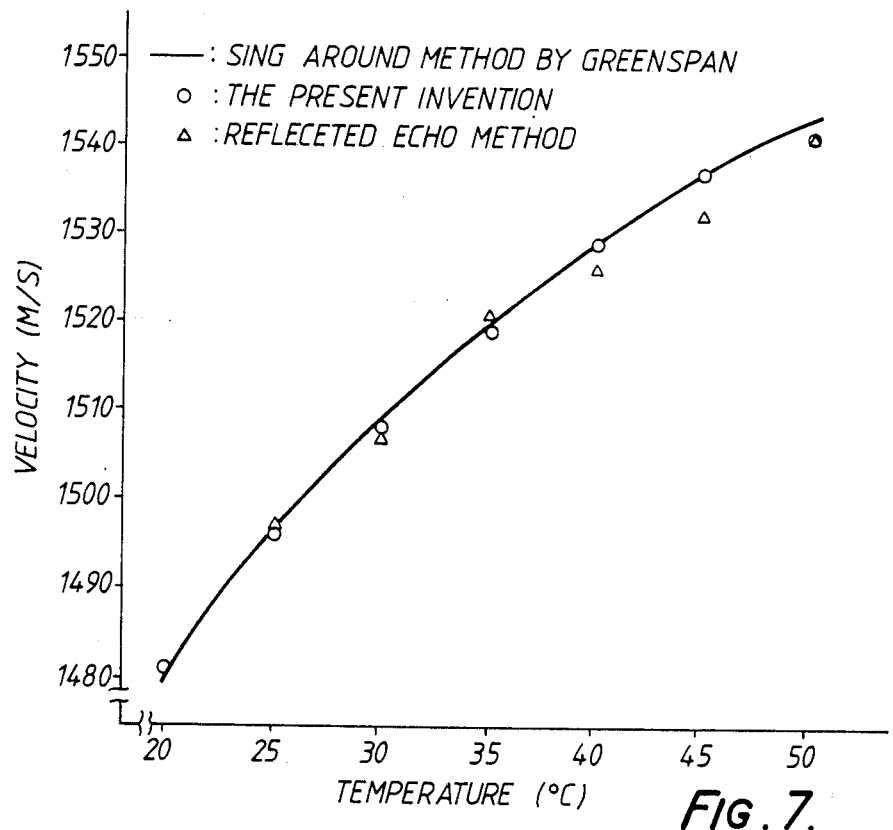
FIG. 7 is a graph showing the sound velocities measured by the present invention and comparing it with the results achieved by other methods.

In order to verify the accuracy of the system and method of the present invention, the velocity in water with scatteror (0.1 Wt% granular polyethelene was used) was measured and compared with the published data by Greenspan. In order to reduce the speckle noise, 100 raw data results obtained from many different propagation paths in the same medium were averaged. An example of the raw data is shown in FIG. 6. Propagation time T is defined as the time period from driving the transmitting position A until the peak amplitude of scattered echo arrives to the receiving position B. As a comparison, the velocity of the same phantom was measured by the reflected echo method. In that method the time-delay of echoes reflected from 10 wire-targets having spacing of 10 mm and positioned parallel to the propagating direction was measured. The results are summarized in FIG. 7 and show that error of the system and method of the above invention is less than 0.5% in water. In order to verify the effect of attenuation in the medium, the velocity in the homogeneous agar-graphite phantom which has the attenuation of 0.5 dB.cm MHz was measured. The velocity measured by reflected echo method was $1551.2 \pm 2.6$ m/s, and the velocity measured by this system was $1547 \pm 8.0$ m/s.

As described above, it was confirmed that the error of the system and method of the preferred embodiment disclosed herein is less than 0.5%. That error is sufficiently small that the disclosed system and method may be used for the diagnosis of, for example, diffused liver diseases.

What is claimed is:

1. A system for measuring the sound velocity of the tissue of an object to be investigated, the system comprising:
   an array of transducer elements spaced at predetermined intervals for transmitting pulses into the object and receiving echoes of said pulses reflected from said object, said array including a first sub-array of transducers and a distinct second sub-array of transducers, the first and second sub-arrays being separated by a predetermined distance;
   transmitting means coupled with said array for exciting said first sub-array to direct pulses toward said object along a transmitting beam;
   receiving means coupled with said array for activating said second sub-array of transducers to receive echoes of said pulses along a receiving beam;
   beam steering means coupled with said first and second sub-arrays for activating said transducers at phased predetermined time delays to steer at least one of said transmitting beam and said receiving beam at an angle other than ninety degrees so that the transmitting beam and the receiving beam intersect at a point within the tissue;
   time measuring means coupled with said first and second sub-arrays for measuring the propagation time between the moment a given pulse is transmitted by the first sub-array along the transmitting beam and the moment the echo of the pulse is received by the second sub-array along the receiving beam; and,
   computing means coupled with said beam steering means and said time measuring means for determining the sound velocity of the tissue from the measured propagation time, the predetermined spaced intervals, the predetermined distance, and the predetermined time delays.

2. The system of claim 1 wherein said time measuring means includes a memory device.

3. The system of claim 1 further comprising an averaging means coupled with said time measuring means for storing and averaging a plurality of propagation times measured by said time measuring means.

4. A system for measuring the sound velocity of an inner, tissue body within an object to be investigated, the system comprising:
   an array of transducer elements spaced at predetermined intervals for transmitting pulses into the object and receiving echoes of said pulses reflected from said object, said array including at least two sub-arrays of transducers that are separate from one another by a predetermined distance;
   transmitter means coupled with said array for exciting a sub-array of transducers to direct pulses toward said object along a transmitting beam;
   receiving means coupled with said array for activating a sub-array of transducers different than those activated by the transmitting means to receive echoes of said pulses along a receiving beam;
   beam steering means coupled with at least one sub-array for activating transducers of that sub-array at phased predetermined time delays to steer at least one of a given transmitting beam and a given receiving beam so that the pair of beams intersect at a point within the object;
   means for producing a first pair of a transmitting beam and a receiving beam which intersect at a point Po within the tissue of the inner tissue body;
   means for propagating a second pair of a transmitting beam and a receiving beam which intersect at a point P1 proximate the outer periphery of the inner tissue body so that the transmitting beam and the receiving beam do not travel through the inner body tissue;
   time measuring means coupled with said sub-arrays for measuring the propagation time taken for a particular pulse to travel along a given pair of transmitting and receiving beams to and from the phased array and for thereby determining a first propagation time for the first pair of beams which intersect at P0 and a second propagation time for the second pair of beams which intersect at P1; and, computing means coupled with said beam steering means and said time measuring means for determining the sound velocity of the inner body tissue from the measured first and second propagation times, the predetermined spaced intervals, the distances between the sub-arrays that provide the first and second pair of transmitting and receiving beams, and the predetermined time delays.

5. The system of claim 4 further comprising a sub-array shifting means for shifting at least one of the sub-arrays to thereby provide a second pair of sub-arrays to produce the second pair of transmitting and receiving beams.

6. The system of claim 4 wherein said computing means determines the sound velocity of the inner tissue body as a function of the difference between the first and second propagation times.

7. A method for measuring the sound velocity of an inner tissue body within an object to be investigated, the method comprising the steps of:

directing from a first predetermined position first ultrasonic transmitting beam into the object so that the first transmitting beam passes through at least a portion of the inner body tissue;

receiving to a second predetermined position the ultrasonic pulses reflected from said object along an ultrasonic receiving beam steered to cross the path of said transmitting beam at a first intersection point P0 within the tissue of the inner tissue body;

transmitting from a third predetermined position a second ultrasonic transmitting beam into the object so that the second transmitting beam is directed toward the inner tissue body;

receiving to a fourth predetermined position the ultrasonic pulses reflected from said object along an ultrasonic receiving beam steered to cross the path of said transmitting beam at a second intersection point P1 positioned outside said inner tissue body and spaced a predetermined distance from said first point P0;

measuring the propagation time taken for a pulse to travel along a given intersecting pair of transmitting and receiving beams to and from the respective predetermined positions and thereby determine a first propagation time for the first pair of beams and a second propagation time for a second paid of beams; and computing from the first and second propagation times the sound velocity of the inner body tissue.

8. The method of claim 7 further comprising the steps measuring a number of propagation times to the intersection points P0 and P1 and averaging a plurality of those propagation times.

9. The method of claim 7 wherein said first predetermined position and said third predetermined position are the same.

10. The method of claim 9 wherein said second predetermined position and said fourth predetermined position are the same.

11. The method of claim 7 wherein said first predetermined position and said third predetermined position are different.

12. The method of claim 7 wherein said second predetermined position and said fourth predetermined position are different.

13. The method of claim 7 wherein said second transmitting beam and said second receiving beam are steered to intersect so that point P1 is located at a point proximate the outer periphery of the inner tissue body.

14. The method of claim 7 or 13 wherein said first transmitting beam and said first receiving beam are steered to travel through most of the inner tissue body.

15. The system of claim 1 wherein the computing means determines the sound velocity of the tissue according to the equation $$C = \sqrt{y \cdot d/T \cdot \tau_0}$$

where y is the predetermined distance, d is the predetermined spaced interval, T is the measured propagation time, and $\tau_o$ is the predetermined time delay.

* * * * *